United States Patent
Kanemoto

(10) Patent No.: US 10,328,006 B2
(45) Date of Patent: *Jun. 25, 2019

(54) W/O TYPE EMULSION AND A PREMIX FOR PRODUCING THE SAME

(71) Applicant: Kokyu Alcohol Kogyo Co., Ltd., Narita-shi, Chiba (JP)

(72) Inventor: Mitsu Kanemoto, Narita (JP)

(73) Assignee: Kokyu Alcohol Kogyo Co., Ltd., Narita-shi, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/020,112

(22) Filed: Jun. 27, 2018

(65) Prior Publication Data

US 2018/0369101 A1    Dec. 27, 2018

Related U.S. Application Data

(63) Continuation of application No. 15/823,711, filed on Nov. 28, 2017, now Pat. No. 10,045,922.

(30) Foreign Application Priority Data

May 30, 2017 (JP) ................................ 2017-106727

(51) Int. Cl.
| | |
|---|---|
| *A61K 8/44* | (2006.01) |
| *A61K 8/42* | (2006.01) |
| *A61K 8/06* | (2006.01) |
| *A61K 8/36* | (2006.01) |
| *A61Q 19/00* | (2006.01) |

(52) U.S. Cl.
CPC .............. *A61K 8/442* (2013.01); *A61K 8/064* (2013.01); *A61K 8/361* (2013.01); *A61K 8/42* (2013.01); *A61Q 19/00* (2013.01)

(58) Field of Classification Search
CPC .......... A61K 8/442; A61K 8/42; A61K 8/064; A61K 8/361; A61Q 19/00
See application file for complete search history.

(56) References Cited

U.S. PATENT DOCUMENTS

| | | |
|---|---|---|
| 8,617,525 B2 | 12/2013 | Yoshida |
| 10,045,922 B1 | 8/2018 | Kanemoto |
| 2010/0166684 A1 | 7/2010 | Kokeguchi |

FOREIGN PATENT DOCUMENTS

| | | |
|---|---|---|
| EP | 2298274 A1 | 3/2011 |
| EP | 2343044 A1 | 7/2011 |
| EP | 2374447 A1 | 10/2011 |
| JP | 2015227302 A | 12/2015 |
| WO | WO 2009/139092 A1 | 11/2009 |
| WO | WO 2010/037882 A1 | 4/2010 |
| WO | WO 2010/073548 A1 | 7/2010 |
| WO | WO 2012/091823 A1 | 7/2012 |
| WO | WO 2013/170419 A1 | 11/2013 |
| WO | WO 2018/079568 A2 | 5/2018 |

OTHER PUBLICATIONS

Exfoliating Oil. ID No. 4624631. Database at http://www.gnpd.com, Feb. 2017.

*Primary Examiner* — Trevor Love
(74) *Attorney, Agent, or Firm* — Wolf, Greenfield & Sacks, P.C.

(57) ABSTRACT

[Problem]
To provide a novel emulsion, and a premix for producing the same.
[Solution]
An water-in-oil type emulsion and a premix, comprising dibutyl lauroyl glutamide, dibutyl ethylhexanoyl glutamide and a fatty acid.

5 Claims, 6 Drawing Sheets

[Fig. 1]
Viscoelasticity measurement result of Control B.
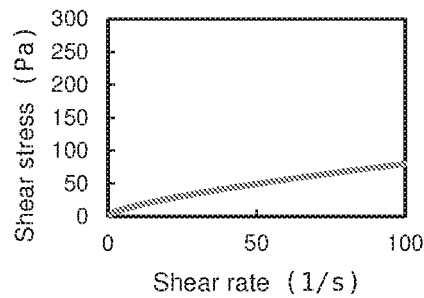
[Fig. 2]
Viscoelasticity measurement result of Example B1 (AJK-IS: 1%).
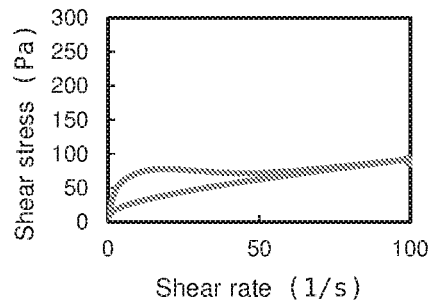
[Fig. 3]
Viscoelasticity measurement result of Example B2 (AJK-IS: 0.5%).
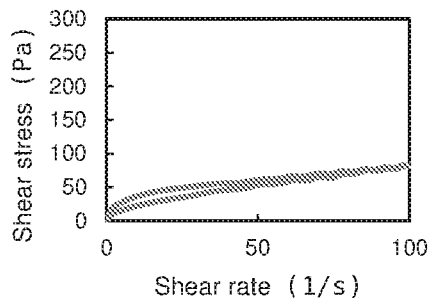

[Fig. 4]
Viscoelasticity measurement result of Comparative Example B1 (GP-1 + EB-21).
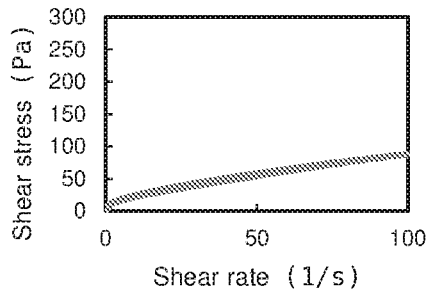
[Fig. 5]
Viscoelasticity measurement result of Comparative Example B2 (GP-1).
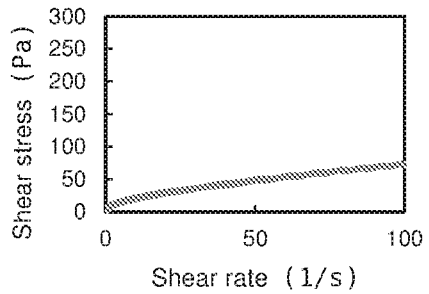
[Fig. 6]
Viscoelasticity measurement result of Comparative Example B3 (EB-21).
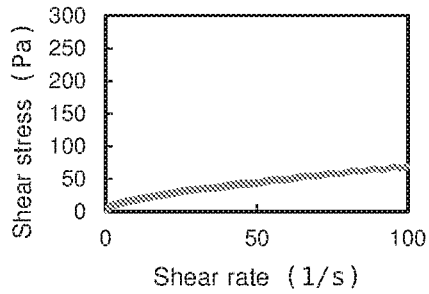

[Fig. 7]
Viscoelasticity measurement result of Comparative Example B4 (Isostearic acid + GP-1).
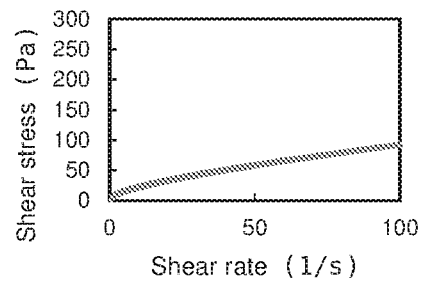
[Fig. 8]
Viscoelasticity measurement result of Comparative Example B5 (Isostearic acid + EB-21).
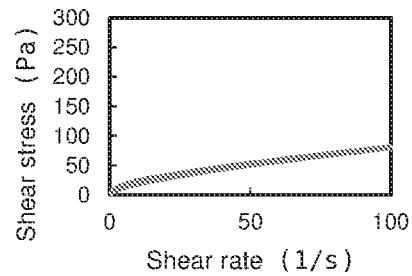
[Fig. 9]
Viscoelasticity measurement result of Comparative Example B6 (Isostearic acid).
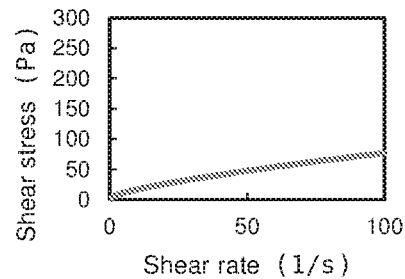

[Fig. 10]
Viscoelasticity measurement result of Example B1 after one month of storage.
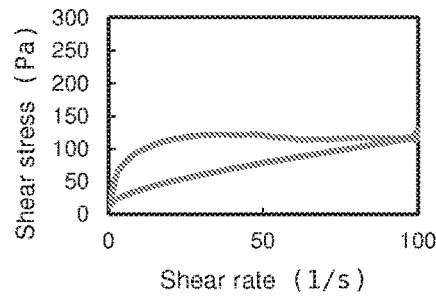
[Fig. 11]
Viscoelasticity measurement result of Example B2 after one month of storage.
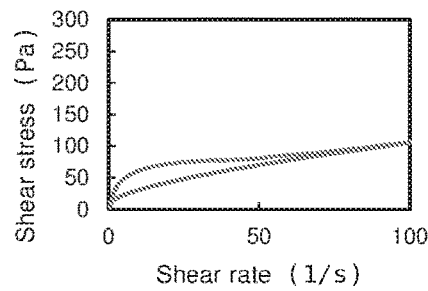
[Fig. 12]
Viscoelasticity measurement result of Control C.
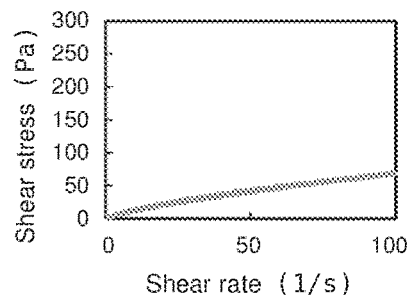

[Fig. 13]
Viscoelasticity measurement result of Example C1.
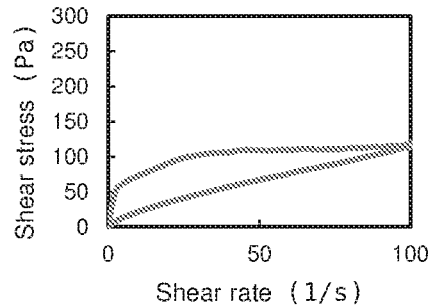
[Fig. 14]
Viscoelasticity measurement result of Example C2.
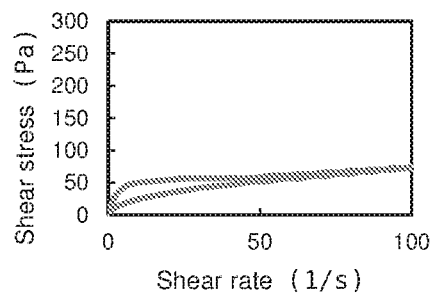
[Fig. 15]
Viscoelasticity measurement result of Example D1.
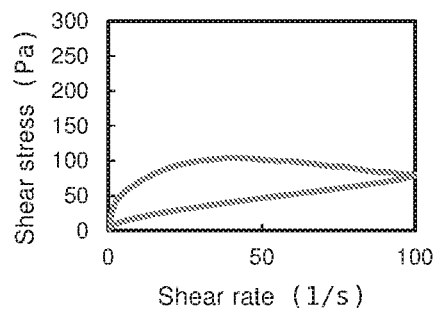

[Fig. 16]
Viscoelasticity measurement result of Example D2.
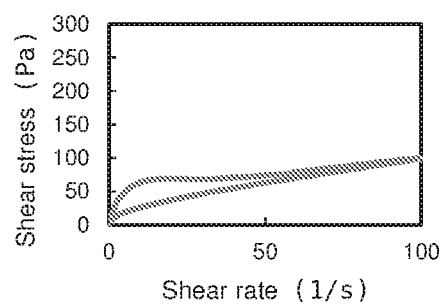

W/O TYPE EMULSION AND A PREMIX FOR PRODUCING THE SAME

RELATED APPLICATION

This application is a continuation of U.S. application Ser. No. 15/823,711, filed Nov. 28, 2017, the entire content of which is incorporated herein by reference in its entirety.

TECHNICAL FIELD

The present invention relates to a W/O type emulsion and a premix for producing the same.

BACKGROUND ART

Conventionally, dibutyl lauroyl glutamide and dibutyl ethylhexanoyl glutamide have been known as an oil gelling agent used in the production of cosmetics, and they have been used in the production of oily cosmetics such as lipstick and lip gloss (Patent Document 1). In addition, the use of dibutyl lauroyl glutamide and dibutyl ethylhexanoyl glutamide in water-in-silicone oil type emulsions or water-in-oil type emulsified cosmetics has also been studied (Patent Document 2, Patent Document 3).

CITATION LIST

Patent Document

[Patent Document 1] WO 2009/139092 A
[Patent Document 2] WO 2012/091823 A
[Patent Document 3] WO 2010/073548 A

SUMMARY OF THE INVENTION

Problems to be Solved by the Invention

The inventor of the present invention has worked on research to provide a novel emulsion and a premix for producing the same.

Means of Solving the Problems

The present inventor has conducted intensive studies, and found that an emulsion having storage stability can be obtained by preparing a W/O type emulsion by means of combining dibutyl lauroyl glutamide and dibutyl ethylhexanoyl glutamide with a specific fatty acid; as a result of further research, the present inventors have completed the present invention.

[1] A W/O type emulsion comprising dibutyl lauroyl glutamide, dibutyl ethylhexanoyl glutamide, and a fatty acid.
[2] The emulsion according to [1], comprising dibutyl lauroyl glutamide in an amount of 0.13-0.85%.
[3] The emulsion according to [1] or [2], comprising dibutyl ethylhexanoyl glutamide in an amount of 0.04-0.30%.
[4] The emulsion according to any one of [1] to [3], comprising a fatty acid in an amount of 0.3-3.0%.
[5] The emulsion according to any one of [1] to [4], wherein the fatty acid is isostearic acid.
[6] The emulsion according to any one of [1] to [5], which is an external preparation.
[7] The emulsion according to [6], which is a cosmetic product.
[8] A premix for W/O type emulsion comprising dibutyl lauroyl glutamide, dibutyl ethylhexanoyl glutamide, and a fatty acid.
[9] The premix according to [8], consisting of dibutyl lauroyl glutamide, dibutyl ethylhexanoyl glutamide, and a fatty acid.
[10] The premix according to [8] or [9], wherein the weight ratio of fatty acid:dibutyl lauroyl glutamide:dibutyl ethylhexanoyl glutamide is 40-75:15-40:5-40.
[11] A W/O type emulsion comprising the premix according to [10] in an amount of 0.3-3.0 wt %.
[12] The emulsion according to [11], which is a cosmetic product.
[13] A method for producing a W/O type emulsion, comprising adding the premix according to any one of [8] to [10] to an oily ingredient, and emulsifying it with an aqueous ingredient.

Advantageous Effects of the Invention

By combining dibutyl lauroyl glutamide, dibutyl ethylhexanoyl glutamide and a fatty acid, separation was prevented, and a W/O type emulsion having storage stability could be provided. Accordingly, the present invention can provide a W/O type emulsion of various forms such as milk form and cream form which is excellent in storage stability.

Furthermore, by combining dibutyl lauroyl glutamide, dibutyl ethylhexanoyl glutamide and a fatty acid, a W/O type emulsion having a characteristic texture could be provided.

In general, emulsions with high viscosity have a certain weight and hardness at the beginning of application, so that it is easy to take them with fingertips and to apply them to the skin; however, due to their hard texture, it is difficult to spread them on the skin, and their slipperiness tends to be inferior. Meanwhile, emulsions with low viscosity are excellent in spreadability and slipperiness; however, because of their soft texture, it is difficult to take them with fingertips, and they tend to drip off at the start of application, and coating sensation and moisturizing feel after application tend to be low. In contrast, the W/O type emulsion of the present invention having excellent slipperiness in addition to a certain weight and hardness at the beginning of application can be said to have a distinctive texture and usability. These emulsions show such a distinctive viscoelastic behavior (humped curve) in a graph of viscoelasticity measurement.

In addition, emulsions, in particular emulsions containing a gelling agent, may increase in viscosity over time, and may be required to be stored for approximately one month before shipment for marketing in order to control product quality; this process is called an aging step. The W/O type emulsions of the present invention also have the advantage that the change over time is relatively small and the aging step can be shortened, or, there is no need to have an aging step.

In one embodiment of the present invention, it is preferable that the W/O type emulsion shows a distinctive viscoelastic behavior (humped curve) immediately after the production of the emulsion, which does not change greatly even after one week or one month.

In another embodiment of the present invention, it is preferable that the W/O type emulsion shows a distinctive viscoelastic behavior (humped curve) within one week from the production of the emulsion, which does not change greatly even after one month from the production.

In addition, the present invention enabled to provide a premix product suitable for producing a W/O type emulsion as a premix containing dibutyl lauroyl glutamide, dibutyl ethylhexanoyl glutamide and a fatty acid.

BRIEF DESCRIPTION OF DRAWINGS

FIG. 1 is a graph showing viscoelasticity of Control B.
FIG. 2 is a graph showing viscoelasticity of Example B1.
FIG. 3 is a graph showing viscoelasticity of Example B2.
FIG. 4 is a graph showing viscoelasticity of Comparative Example B1.
FIG. 5 is a graph showing viscoelasticity of Comparative Example B2.
FIG. 6 is a graph showing viscoelasticity of Comparative Example B3.
FIG. 7 is a graph showing viscoelasticity of Comparative Example B4.
FIG. 8 is a graph showing viscoelasticity of Comparative Example B5.
FIG. 9 is a graph showing viscoelasticity of Comparative Example B6.
FIG. 10 is a graph showing viscoelasticity of Example B1 after one month of storage.
FIG. 11 is a graph showing viscoelasticity of Example B2 after one month of storage.
FIG. 12 is a graph showing viscoelasticity of Control C.
FIG. 13 is a graph showing viscoelasticity of Example C1.
FIG. 14 is a graph showing viscoelasticity of Example C2.
FIG. 15 is a graph showing viscoelasticity of Example D1.
FIG. 16 is a graph showing viscoelasticity of Example D2.

DETAILED DESCRIPTION OF THE INVENTION

<W/O Type Emulsion>

A "W/O type emulsion" is a water-in-oil type emulsion, namely, an emulsion in which an aqueous ingredient is dispersed in a continuous phase containing an oily ingredient.

In one embodiment of the present invention, the W/O type emulsion can be used for any purpose, but typically it can be used for external preparations such as pharmaceutical products, quasi-drugs, cosmetic products, etc. Since the emulsion of the present invention has a distinctive texture, and has a characteristic usability at the time of application, it is preferably used for external preparations for the skin. In one embodiment of the present invention, the W/O type emulsion is preferably a cosmetic product, particularly preferably a cosmetic product for the skin.

The W/O type emulsion of the present invention can be used in various forms of products including pharmaceutical products such as a skin external preparation containing a medicament; quasi drugs such as medicated cosmetics; skin care cosmetic products such as gel lotion, milky lotion, cream, sunscreen, daytime moisturizing agent, etc.; makeup cosmetic products such as foundation, makeup base, eye shadow, mascara, etc.

<Premix for W/O Type Emulsion>

The "premix for W/O type emulsion" of the present invention is a mixture containing dibutyl lauroyl glutamide, dibutyl ethylhexanoyl glutamide and a fatty acid, and is a raw material for use in the production of a W/O type emulsion. It is also referred to as "premix" in this specification.

It goes without saying that dibutyl lauroyl glutamide, dibutyl ethylhexanoyl glutamide and a fatty acid can be mixed as individual raw materials in the production of a W/O type emulsion of the present invention, but it is advantageous to prepare a premix of blended and melted dibutyl lauroyl glutamide and dibutyl ethylhexanoyl glutamide in combination with a fatty acid, because this facilitates the blending of dibutyl lauroyl glutamide and dibutyl ethylhexanoyl glutamide at the time of production of a W/O type emulsion such as an external preparation.

Accordingly, the present invention also provides a method for producing a W/O type emulsion, comprising adding the premix to an oily ingredient containing an oil agent.

In one embodiment of the present invention, the premix may comprise other ingredients, for example other oil agents.

In one embodiment of the present invention, the premix consists substantially of dibutyl lauroyl glutamide, dibutyl ethylhexanoyl glutamide and a fatty acid. "Substantially" as used herein means that components such as impurities that do not significantly affect the properties of the present invention may be included.

<Dibutyl Lauroyl Glutamide (GP-1)>

Dibutyl lauroyl glutamide is an amino-acid based oil gelling agent, and is commercially available under the product name "GP-1 (ingredient name: N-lauroyl-L-glutamic acid dibutylamide)" (from Ajinomoto Co., Inc.). In the present specification, dibutyl lauroyl glutamide is also referred to as "GP-1".

The blending amount of dibutyl lauroyl glutamide in the W/O type emulsion can be appropriately adjusted depending on the required viscosity, etc., and is not particularly limited; from the viewpoint of preparing preparations showing distinctive viscoelastic behavior of the present invention, it may be 0.13-0.85 wt %, preferably 0.20-0.70 wt %, and more preferably 0.25-0.55 wt %.

The blending amount of dibutyl lauroyl glutamide in the premix is not particularly limited; from the viewpoint of ease of handling as a premix in the preparation of cosmetics and the like, it may be 15-40 wt %, preferably 15-36 wt %, and more preferably 20-30 wt %.

<Dibutyl Ethylhexanoyl Glutamide (EB-21)>

Dibutyl ethylhexanoyl glutamide is an amino-acid based oil gelling agent, and is commercially available under the product name "EB-21 (ingredient name: N-2-ethylhexanoyl-L-glutamic acid dibutylamide)" (from Ajinomoto Co., Ltd.).

The blending amount of dibutyl ethylhexanoyl glutamide in the W/O type emulsion can be appropriately adjusted depending on the required viscosity, etc., and is not particularly limited; from the viewpoint of preparing preparations showing distinctive viscoelastic behavior of the present invention, it may be 0.04-0.30 wt %, preferably 0.05-0.20 wt %, and more preferably 0.07-0.10 wt %.

The blending amount of dibutyl ethylhexanoyl glutamide in the premix is not particularly limited; from the viewpoint of ease of handling as a premix in the preparation of cosmetics and the like, it may be 5-40 wt %, preferably 5-20 wt %, more preferably 5-10 wt %, and even more preferably 7-10 wt %.

<Fatty Acid>

The fatty acid used in the present invention is not particularly limited, and may be used singly or in combination of a plurality of fatty acids.

In one embodiment of the present invention, from the viewpoint of using the W/O type emulsion as an external preparation, a higher fatty acid (fatty acid having 12 or more carbon atoms) is preferable.

Examples of the higher fatty acid include lauric acid, myristic acid, palmitic acid, stearic acid, isostearic acid, oleic acid, behenic acid, linoleic acid, linolenic acid, arachidonic acid, eicosapentaenoic acid (EPA), docosahexaenoic acid (DHA), isostearic acid and the like.

In a preferred embodiment of the present invention, the fatty acid is a fatty acid selected from C12-C22 fatty acids, and is particularly preferably a C12-C18 saturated fatty acid, and most preferably isostearic acid.

From the viewpoint of use for a wide range of cosmetic products, the viewpoint of versatility as a premix, or the viewpoint of stability over time, isostearic acid is preferable.

The blending amount of the fatty acid in the W/O type emulsion is not particularly limited; from the viewpoint of preparing preparations showing distinctive viscoelastic behavior of the present invention, it may be 0.3-3.0 wt %, preferably 0.3-2.0 wt %, and more preferably 0.5-1.5 wt %.

The blending amount of the fatty acid in the premix is not particularly limited; from the viewpoint of ease of handling as a premix in the preparation of cosmetics and the like, it may be 40-75 wt %, preferably 50-70 wt %, and more preferably 60-70 wt %.

<Ratio>

The ratio of dibutyl lauroyl glutamide (GP-1), dibutyl ethylhexanoyl glutamide (EB-21) and fatty acid in the W/O type emulsion and in the premix of the present invention is not particularly limited; it can be selected appropriately depending on the application to be aimed, desired viscosity of the emulsion and the like.

In one embodiment of the present invention, from the viewpoint of preparing preparations showing distinctive viscoelastic behavior of the present invention, the weight ratio of the fatty acid:GP-1:EB-21 is 40-75:15-40:5-40, preferably 50-70:15-36:5-20, and more preferably 60-70:20-30:5-10.

<Blending Amount of the Premix>

In the present invention, the blending amount of the premix in the W/O type emulsion is not particularly limited, and can be appropriately selected depending on the desired viscosity and hardness of the W/O type emulsion of interest.

In one embodiment of the present invention, from the viewpoint of usability as an external preparation, the blending amount of the premix in the W/O type emulsion is preferably 0.3-3.0 wt %, more preferably 0.3-2.0 wt %, and still more preferably 0.5-1.5 wt %.

In another aspect of the present invention, from the viewpoint of preparing preparations showing distinctive viscoelastic behavior of the present invention, the blending amount of the premix in the W/O type emulsion is preferably 0.5-3.0 wt %, more preferably 0.6-2.0 wt %, and still more preferably 0.7-1.5 wt %.

In still another embodiment of the present invention, from the viewpoint of storage stability, the blending amount of the premix in the W/O type emulsion is 0.3 wt % or more, preferably 0.4 wt % or more, and more preferably 0.5 wt %.

<Oily Ingredient>

The oily ingredient used in the W/O type emulsion of the present invention is not particularly limited as long as it is an ingredient generally used in cosmetics and the like, and examples thereof include animal and vegetable fats and oils, hydrocarbon oils, higher fatty acids, higher alcohols, ester oil, silicone oil and the like, and these can be used alone or in combination of two or more kinds.

Examples of animal and vegetable fat and oil or hydrogenated animal and vegetable fats and oils include avocado oil, eno oil, olive oil, cacao butter, kaya oil, apricot kernel oil, hardened oil, wheat germ oil, sesame oil, rice germ oil, rice bran oil, sugarcane wax, sasanqua oil, safflower oil, shea butter, Chinese tung oil, cinnamon oil, soybean oil, tea seed oil, camellia oil, evening primrose oil, corn oil, rapeseed oil, germ oil, palm oil, palm kernel oil, castor oil, hardened castor oil, sunflower oil, grape oil, jojoba oil, macadamia nut oil, beeswax, cottonseed oil, cotton wax, Japan wax, montan wax, coconut oil, hardened coconut oil, peanut oil, lanolin, liquid lanolin, reduced lanolin, lanolin alcohol, hard lanolin, lanolin acetate, lanolin fatty acid isopropyl ester, hexyl laurate and the like.

Examples of hydrocarbon oil include ozokerite, squalane, squalene, ceresin, paraffin, isoparaffin, paraffin wax, liquid paraffin (mineral oil), pristane, polyisobutylene, polyisobutene, hydrogenated polyisobutene, microcrystalline wax, polyethylene wax, vaseline and the like.

Examples of higher fatty acid include lauric acid, myristic acid, palmitic acid, stearic acid, isostearic acid, oleic acid, behenic acid, undecylenic acid, oleic acid, linoleic acid, linolenic acid, arachidonic acid, eicosapentaenoic acid (EPA), docosahexaenoic acid (DHA), isostearic acid and the like.

Examples of higher alcohol include myristyl alcohol, cetanol, stearyl alcohol, arachidyl alcohol, behenyl alcohol, hydrogenated rapeseed oil alcohol and the like.

Examples of ester oil include as follows: as a monoester, isononanoate such as isononyl isononanoate, isotridecyl isononanoate, etc.; 2-ethylhexanoate such as cetyl ethylhexanoate, hexyldecyl ethyl hexanoate, etc.; myristate such as isopropyl myristate, isocetyl myristate, octyldodecyl myristate, etc.; isostearate such as ethyl isostearate, isopropyl isostearate, hexyldecyl isostearate, isostearyl isostearate, cholesteryl isostearate, phytosteryl isostearate, etc.; lactate such as isostearyl lactate, octyldodecyl lactate, etc.; oleate such as oleyl oleate, phytosteryl oleate, octyldodecyl oleate, etc.; neopentanoate such as isodecyl neopentanoate, isostearyl neopentanoate, etc.; palmitate such as isopropyl palmitate, ethylhexyl palmitate, etc.; in addition, octyldodecyl neodecanoate, octyldodecyl ricinoleate, oleyl erucate, octyldodecyl erucate, isopropyl lauroyl sarcosine, etc.

Examples of diester oil include diisobutyl adipate, diisopropyl adipate, diethylhexyl succinate, neopentyl glycol diisononanoate, neopentyl glycol diethylhexanoate, neopentyl glycol dicaprate, diisostearyl malate, diisopropyl dilinoleate, ethylene glycol dioctoate, octyldodecyl stearoyl oxystearate, diisopropyl sebacate, di(cholesteryl/octyldodecyl) lauroylglutamate, di(phytosteryl/octyldodecyl) lauroylglutamate and the like.

Examples of triester oil include triethylhexanoin, trimethylolpropane triethylhexanoate, glyceryl tri(caprylate/caprate), triisostearin, trimethylolpropane triisostearate and the like.

Examples of tetraester oil include pentaerythrityl tetraethylhexanoate, pentaerythrityl tetraisostearate and the like.

Examples of polyester oil include polyglyceryl fatty acid esters such as polyglyceryl-2 isostearate, polyglyceryl-2 diisostearate, polyglyceryl-2 triisostearate, polyglyceryl-2 tetraisostearate and the like.

Examples of high-viscosity ester oil include hydrogenated castor oil isostearate, hydrogenated castor oil dimer dilinoleate, (polyglyceryl-2 isostearate/dimer dilinoleate) copolymer, (phytosteryl/isostearyl/cetyl/stearyl/behenyl) dimer dilinoleate, dimer dilinoleyl bis (phytosteryl/behenyl/isostearyl) dimer dilinoleate, di(isostearyl/phytosteryl) dimer dilinoleate, dimer dilinoleyl-hydrogenated rosin condensate, dimer dilinoleyl diisostearate, dimer dilinoleyl dimer dilinoleate, di(cholesteryl/behenyl/octyldodecyl) lauroylglutamate, di(octyldodecyl/phytosteryl/behenyl) lauroylglutamate, myristoylmethylalanine (phytosteryl/decyltetradecyl) and the like.

Examples of silicone oil include dimethylpolysiloxane, methylphenylpolysiloxane, alkyl-modified organopolysiloxane, terminal modified organopolysiloxane, fluorine-modified organopolysiloxane, amodimethicone, amino-modified organopolysiloxane, volatile silicone, alkyl dimethicone, cyclopentasiloxane and the like.

In one embodiment of the present invention, from the viewpoint of having many practical use in external preparations and formulation favorable to consumers, it is preferable to use an oil agent such as hydrocarbon oil or vegetable oil, and these can be appropriately combined.

In another embodiment of the present invention, from the viewpoint of light feeling and alleviation of oily feeling (stickiness etc.), it is preferable to use silicone oil and it is also preferable to use it in combination with other oil agent.

In one embodiment of the present invention, the blending amount of the oily ingredient in the W/O type emulsion is not particularly limited; from the viewpoint of preparing preparations showing distinctive viscoelastic behavior of the present invention, it may be 15-55 wt %, preferably 15-40 wt %, and more preferably 15-30 wt %.

In another embodiment of the present invention, the blending amount of the oily ingredient in the W/O type emulsion is not particularly limited; from the viewpoint of usability as an external preparation, it may be 15-55 wt %, preferably 15-50 wt %, and more preferably 15-40 wt %.

<Aqueous Ingredient>

Aqueous ingredients used in the W/O type emulsion of the present invention are not particularly limited as long as it is an ingredient generally used in cosmetic products, etc.; examples thereof include water such as purified water and ion exchanged water; lower alcohols such as BG (1,3-butylene glycol), PG (propylene glycol), glycerin, ethanol, etc., and these can be used singly or in combination of two or more kinds.

In one embodiment of the present invention, the blending amount of the aqueous ingredient in the W/O type emulsion is not particularly limited; from the viewpoint of usability as an external preparation, it may be 50-88 wt %, preferably 60-85 wt %, and more preferably 65-82 wt %.

<Surfactant>

As the surfactant, a surfactant (emulsifier) suitable for W/O type emulsions can be appropriately selected; examples thereof include steareth-11, polyglyceryl-3 diisostearate, polyglyceryl-2 triisostearate, PEG-60 hydrogenated castor oil, PEG-30 glyceryl triisostearate, lauryl PEG-9 polydimethylsiloxyethyl dimethicone, and the like.

It goes without saying that a person skilled in the art can appropriately select the kind, combination and blending amount of the surfactant depending on the type and blending ratio of other ingredients to be used such as an oil agent.

<Other Ingredients>

The emulsion of the present invention may contain any ingredients used in external preparations such as cosmetic products and others.

Examples of these additional ingredients include ultraviolet absorbers such as ethylhexyl methoxycinnamate, hexyl diethylaminohydroxybenzoylbenzoate, etc.; additional thickeners/gelling agents such as (acrylates/alkyl (C10-30) acrylates) crosspolymer, dextrinpalmitate, xanthan gum, etc.; ingredients for maintaining quality such as antioxidants and antiseptics; medicated ingredients and active ingredients such as whitening agent, anti-wrinkle agent, antioxidant, etc.; fragrance and the like.

<Method of Producing the W/O Type Emulsion>

The W/O type emulsion of the present invention can be prepared by a conventional method. For example, it can be prepared by emulsifying each of the aqueous ingredient and oily ingredient in a warmed state and then stirring and cooling to room temperature.

In one embodiment of the present invention, when the premix is used, the W/O type emulsion can be prepared by mixing the premix with an oily ingredient such as an oil agent, and emulsifying the resulting mixture with an aqueous ingredient. More specifically, it can be prepared by dissolving the premix, adding/mixing with a heated oily ingredient such as oil agent, and emulsifying the resulting mixture with an aqueous ingredient.

<Method of Producing the Premix>

The premix of the present invention can be prepared by a conventional method. For example, it can be prepared by dissolving and mixing each ingredient.

Hereinafter, the present invention is described in more detail based on examples; however, the present invention is not limited to these examples, and various modifications can be made without departing from the technical idea of the present invention. In the present specification, unless otherwise specified, % means wt %.

EXAMPLES

Test Example 1

A W/O type emulsion of each sample with the formulation shown in Table 1 was prepared by a conventional method.

TABLE 1

| Product name | Ingredients labelling name | Control A | Example A |
|---|---|---|---|
| Hicall K-230 | Mineral oil | 15 | 15 |
| Eco oil RS | Jojoba oil | 1 | 1 |
| Emalex 611 | Steareth-11 | 0.5 | 0.5 |
| Risocast PGIS 32 | Polyglyceryl-3 diisostearate | 1.5 | 1.5 |
| AJK-IS3613*[1] | Isostearic acid/dibutyl lauroyl glutamide/dibutyl ethylhexanoyl glutamide | — | 1.2 |
| Purified water | Water | 74 | 72.8 |
| BG | BG | 5 | 5 |
| Triol VE | Glycerin | 3 | 3 |

AJK-IS3613(*1)

A solid premix containing the following:
Isostearic acid (product name: isostearic acid EX) 64.0%
Dibutyl lauroyl glutamide (product name: GP-1) 27.0%
Dibutyl ethylhexanoyl glutamide (product name: EB-21) 9.0%

The sample of Example A which contains the premix of isostearic acid/dibutyl lauroyl glutamide/dibutyl ethylhexanoyl glutamide (AJK-IS3613) had a higher viscosity, and sufficient hardness and weight when it was taken at the fingertip (at the start of application), and it had excellent spreadability and slipperiness to the skin, compared to a control without the premix.

In addition, each sample was placed in a glass container and a cycle test (4-45° C.) was conducted to evaluate the presence or absence of separation. As a result, the control sample showed separation after 4 days, whereas the Example sample showed no separation even after one month and was confirmed to have excellent storage stability.

Test Example 2

W/O type emulsions of the formulation shown in Table 2 were each prepared by a conventional method, and the influence by a combination of an amino-acid oil gelling agent and isostearic acid was evaluated.

TABLE 2

Combination of amino-acid oil gelling agent (GP-1 and EB-21) and isostearic acid

| Product name | Ingredients labelling name | Control B | Example B1 | Example B2 | Comp Ex. B1 | Comp Ex. B2 | Comp Ex. B3 | Comp Ex. B4 | Comp Ex. B5 | Comp Ex. B6 |
|---|---|---|---|---|---|---|---|---|---|---|
| Hicall K-230 | Mineral oil | 10 | 10 | 10 | 10 | 10 | 10 | 10 | 10 | 10 |
| Olive squalane | Squalane | 5 | 5 | 5 | 5 | 5 | 5 | 5 | 5 | 5 |
| Eco oil RS | Jojoba oil | 1 | 1 | 1 | 1 | 1 | 1 | 1 | 1 | 1 |
| Emalex 611 | Steareth-11 | 0.5 | 0.5 | 0.5 | 0.5 | 0.5 | 0.5 | 0.5 | 0.5 | 0.5 |
| Emalex HC-60 | PEG-60 hydrogenated castor oil | 1 | 1 | 1 | 1 | 1 | 1 | 1 | 1 | 1 |
| Emalex GWIS-330 | PEG-30 glyceryl triisostearate | 1 | 1 | 1 | 1 | 1 | 1 | 1 | 1 | 1 |
| Risorex PGIS 32 | Polyglyceryl-3 diisostearate | 3 | 3 | 3 | 3 | 3 | 3 | 3 | 3 | 3 |
| Isostearic acid EX | Isostearic acid | — | 0.64 | 0.320 | — | — | — | 0.73 | 0.91 | 1 |
| GP-1 | Dibutyl lauroyl glutamide | — | 0.27 | 0.135 | 0.27 | 0.27 | — | 0.27 | — | — |
| EB-21 | Dibutyl ethylhexanoyl glutamide | — | 0.09 | 0.045 | 0.09 | — | 0.09 | — | 0.09 | — |
| Purified water | Water | 70.5 | 69.5 | 70 | 70.14 | 70.23 | 70.41 | 69.5 | 69.5 | 69.5 |
| Highsugarcane BG | BG | 5 | 5 | 5 | 5 | 5 | 5 | 5 | 5 | 5 |
| Triol VE | Glycerin | 3 | 3 | 3 | 3 | 3 | 3 | 3 | 3 | 3 |

Examples B1 and B2 are samples prepared by blending 1% or 0.5% of the same premix as the premix used in Test Example 1 (AJK-IS3613). In Examples B1 and B2 in Table 2, the blending amounts of GP-1, EB-21, and isostearic acid are expressed as converted values.

<Viscoelasticity>

Viscoelasticity of each sample was measured by the following method.
Equipment name: HAAKE RheoStress RS600
Measurement conditions: Cone plate C35 TL010100
Measurement temperature 35° C.

Results of viscoelasticity measurement of each sample are shown in FIGS. 1 to 9.

From these results, it can be understood that the samples containing the combination of three ingredients: GP-1, EB-21 and isostearic acid (a fatty acid) exhibit different viscoelastic behavior from other samples.

Viscoelasticity of Examples B1 and B2 after one month of storage at 25° C. was measured in the same way.

The results are shown in FIGS. 10 and 11.

From these results, it can be understood that the samples of Examples B1 and B2 have little change over time, and there is no need to set an ageing period after production of the W/O type emulsion before shipment as a product.

<Sensory Evaluation>

For Control B and Example B1, usability was evaluated by panelists (7 persons).

A 5-point evaluation was carried out wherein the Control as the median (3) for each item.

Evaluation Items
Weight/hardness at the beginning of application (1: Light/fragile to 5: Heavy/hard)
Strength of coating sensation (1: Weak/thin to 5: Strong/thick)

As a result, in comparison to Control B, Example B1 was improved in terms of spreadability (average 3.29) in addition to weight/hardness at the beginning of application (average 3.86).

The results of these sensory evaluations are also consistent with the physical properties that can be read from a difference in the viscoelastic behavior shown in the viscoelasticity measurement results of FIG. 1 (Control B) and FIG. 2 (Example B1).

Incidentally, in Example B1, the strength of coating sensation was improved and the moisturizing feel was comparable compared to Control B.

In addition, the emulsions of Examples B1 and B2 did not separate even after one month, thus their storage stability was also excellent.

Test Example 3

Each sample of daytime moisturizing agents with the formulation shown in Table 3 was prepared by a conventional method.

TABLE 3

Formulation of daytime moisturizing agent

| Product name | Ingredients labelling name | Control C | Example C1 | Example C2 |
|---|---|---|---|---|
| Hicall K-230 | Mineral oil | 10 | 10 | 10 |
| Squalane | Squalane | 5 | 5 | 5 |
| Eco oil RS | Jojoba oil | 1 | 1 | 1 |
| Risorex PGIS 32 | Polyglyceryl-3 diisostearate | 3 | 3 | 3 |
| Risorex PGIS 23 | Polyglyceryl-2 triisostearate | 3 | 3 | 3 |
| Emalex GWIS-330 | PEG-30 glyceryl triisostearate | 1 | 1 | 1 |
| Emalex HC-60 | PEG-60 hydrogenated castor oil | 1 | 1 | 1 |
| AJK-IS3613*[1] | Isostearic acid/dibutyl lauroyl glutamide/dibutyl ethylhexanoyl glutamide | — | 1 | 0.5 |
| MC80 | Ethylhexyl methoxycinnamate | 3.5 | 3.5 | 3.5 |
| Uvinul A-plus | Hexyl diethylamino hydroxybezoyl-benzoate | 1.5 | 1.5 | 1.5 |
| Purified water | Water | 61.8 | 60.8 | 61.3 |
| Highsugarcane BG | BG | 5 | 5 | 5 |
| Triol VE | Glycerin | 3 | 3 | 3 |
| ULTREZ 21 | (Acrylate/alkyl acrylate (C10-30)) crosspolymer | 0.2 | 0.2 | 0.2 |
| KOH 10% aq | Potassium hydroxide solution (10%) | 1 | 1 | 1 |

In the same manner as in Test Example 2, viscoelasticity measurement of each sample was carried out. Results are shown in FIGS. 12 to 14.

It can be understood that, even in the formulation containing an ultraviolet absorber and an additional gelling agent, distinctive viscoelastic behavior is observed by blending isostearic acid/dibutyl lauroyl glutamide/dibutyl ethylhexanoyl glutamide.

Test Example 4

Using a fatty acid other than isostearic acid, a sample of the formulation shown in Table 4 was prepared in the same manner as in Comparative Example 2, and viscoelasticity was measured. Results are shown in FIGS. 15 and 16.

TABLE 4

Comparison of fatty acids

| Product name | Ingredients labelling name | Example D1 | Example D2 |
|---|---|---|---|
| Hicall K-230 | Mineral oil | 10 | 10 |
| Olive squalane | Squalane | 5 | 5 |
| Eco oil RS | Jojoba oil | 1 | 1 |
| Emalex 611 | Steareth-11 | 0.5 | 0.5 |
| Emalex HC-60 | PEG-60 hydrogenated castor oil | 1 | 1 |
| Emalex GWIS-330 | PEG-30 glyceryl triisostearate | 1 | 1 |
| Risorex PGIS 32 | Polyglyceryl-3 diisostearate | 3 | 3 |
| Lauric acid | Lauric acid | 0.64 | — |
| Palmitic acid | Palmitic acid | — | 0.64 |
| GP-1 | dibutyl lauroyl glutamide | 0.27 | 0.27 |
| EB-21 | dibutyl ethylhexanoyl glutamide | 0.09 | 0.09 |
| Purified water | Water | 69.5 | 69.5 |
| Highsugarcane BG | BG | 5 | 5 |
| Triol VE | Glycerin | 3 | 3 |

INDUSTRIAL APPLICABILITY

As stated above, it is possible to provide a W/O emulsion having storage stability by using a combination of dibutyl lauroyl glutamide, dibutyl ethylhexanoyl glutamide and a fatty acid.

Such emulsions can be used for applications such as cosmetic products.

The invention claimed is:

1. A method for producing a premix for W/O type emulsions consisting of dibutyl lauroyl glutamide, dibutyl ethylhexanoyl glutamide, and isostearic acid, comprising the step of blending the dibutyl lauroyl glutamide, dibutyl ethylhexanoyl glutamide, and isostearic acid to form the premix.

2. The method of claim 1, comprising dibutyl lauroyl glutamide in an amount of 0.13-0.85%.

3. The method of claim 1, comprising dibutyl ethylhexanoyl glutamide in an amount of 0.04-0.30%.

4. The method of claim 1, comprising isostearic acid in an amount of 0.3-3.0%.

5. The method of claim 1, wherein the weight ratio of isostearic acid:dibutyl lauroyl glutamide:dibutyl ethylhexanoyl glutamide is 40-75:15-40:5-40.

* * * * *